US012778964B2

(12) United States Patent
Feifel

(10) Patent No.: US 12,778,964 B2
(45) Date of Patent: Nov. 3, 2026

(54) PSYCHEDELIC DRUG TREATMENT OF NEUROPSYCHIATRIC DISORDERS AND CEREBRAL PALSY

(71) Applicant: David Feifel, La Jolla, CA (US)

(72) Inventor: David Feifel, La Jolla, CA (US)

( * ) Notice: Subject to any disclaimer, the term of this patent is extended or adjusted under 35 U.S.C. 154(b) by 321 days.

(21) Appl. No.: 18/572,498

(22) PCT Filed: Jun. 22, 2022

(86) PCT No.: PCT/US2022/034544
§ 371 (c)(1),
(2) Date: Dec. 20, 2023

(87) PCT Pub. No.: WO2022/271841
PCT Pub. Date: Dec. 29, 2022

(65) Prior Publication Data

US 2025/0195537 A1 Jun. 19, 2025

Related U.S. Application Data

(60) Provisional application No. 63/214,626, filed on Jun. 24, 2021.

(51) Int. Cl.

| | |
|---|---|
| ***A61K 31/5513*** | (2006.01) |
| ***A61K 9/00*** | (2006.01) |
| ***A61K 31/135*** | (2006.01) |
| ***A61P 25/22*** | (2006.01) |

(52) U.S. Cl.
CPC ........ *A61K 31/5513* (2013.01); *A61K 9/0019* (2013.01); *A61K 31/135* (2013.01); *A61P 25/22* (2018.01)

(58) Field of Classification Search
CPC .................................................. A61K 31/5513
See application file for complete search history.

(56) References Cited

U.S. PATENT DOCUMENTS

| | | | |
|---|---|---|---|
| 10,758,532 | B2 | 9/2020 | Kollins et al. |
| 2004/0235956 | A1 | 11/2004 | Quay |
| 2012/0108510 | A1 | 5/2012 | Young et al. |
| 2012/0322736 | A1 | 12/2012 | Yeonmans et al. |
| 2013/0085106 | A1 | 4/2013 | Pedersen et al. |
| 2015/0253305 | A1 | 9/2015 | Moskal |
| 2016/0279054 | A1 | 9/2016 | Rangaramanujam et al. |
| 2020/0171049 | A1 | 6/2020 | Kanes et al. |
| 2021/0322447 | A1 | 10/2021 | Plakogiannis et al. |
| 2021/0386688 | A1 | 12/2021 | Canuso et al. |
| 2025/0099532 | A1 | 3/2025 | Belnap |

FOREIGN PATENT DOCUMENTS

| | | | |
|---|---|---|---|
| EP | 3 570 830 B1 | | 4/2021 |
| WO | WO 2020/188551 | A1 | 9/2020 |
| WO | WO 2020/252384 | A1 | 12/2020 |
| WO | WO2020252384 | * | 12/2020 |
| WO | WO 2022/082058 | A1 | 4/2022 |

OTHER PUBLICATIONS

Lenze, Eric, et al. "96 Hour Infusion of Ketamine for Treatment Resistant Depression: Clinical and Resting State Connectivity Findings", *Biological Psychiatry*, vol. 81, No. 10, May 15, 2017.
Extended European Search Report issued Feb. 13, 2025, in corresponding European Patent Application No. 22829237.1.
Albott et al. "The antidepressant effect of repeat dose intravenous ketamine is delayed by concurrent benzodiazepine use." The Journal of Clinical Psychiatry 78:3 (2017): 1863. e308-e309.
Andrashko et al. "The antidepressant effect of ketamine is dampened by concomitant benzodiazepine medication." Frontiers in psychiatry (2020): 11:844.
Breeksema et al. "Psychedelic treatments for psychiatric disorders: A systematic review and thematic synthesis of patient experiences in qualitative studies." CNS Drugs 34 (2020): 925-946.
Chow et al. "Ketamine-based procedural sedation and analgesia for botulinum toxin A injections in children with cerebral palsy." European Journal of Paediatric Neurology 20.2 (2016): 319-322.
Ford et al. "Benzodiazepines may reduce the effectiveness of ketamine in the treatment of depression." Australian & New Zealand Journal of Psychiatry 49.12 (2015): 1227-1227.
Gülck et al. "Phytocannabinoids: Origins and biosynthesis." Trends in plant science 25.10 (2020): 985-1004.
Hilfiger et al. "A nonpeptide oxytocin receptor agonist for a durable relief of inflammatory pain." Scientific Reports 10.1 (2020): 3017.
International Search Report and Written Opinion dated Nov. 7, 2022, corresponding to PCT Application No. PCT/US2022/034544.
Johnson, Matthew W., and Roland R. Griffiths. "Potential therapeutic effects of psilocybin." Neurotherapeutics 14 (2017): 734-740.
Salloum et al. "Efficacy of intravenous ketamine treatment in anxious versus nonanxious unipolar treatment-resistant depression." Depression and anxiety 36.3 (2019): 235-243.
Schenberg, Eduardo Ekman. "Psychedelic-assisted psychotherapy: a paradigm shift in psychiatric research and development." Frontiers in pharmacology 9 (2018): 733.
Sobota et al. "Oxytocin reduces amygdala activity, increases social interactions, and reduces anxiety-like behavior irrespective of NMDAR antagonism." Behavioral neuroscience 129.4 (2015): 389.
Tullis, Paul. "The rise of psychedelic psychiatry." Nature 589.7843 (2021): 506-509.
Tupper et al. "Psychedelic medicine: a re-emerging therapeutic paradigm." Cmaj 187.14 (2015): 1054-1059.
Alipoor"The effect of ketamine on preventing postpartum depression" J Med Life. (2021) 14(1): 87-92.
Atalay et al., "Antioxidative and Anti-Inflammatory Properties of Cannabidiol", Dec 25, 2019, Antioxidants 2020, 9, 21; doi:10.3390/antiox9010021.

* cited by examiner (Continued)

*Primary Examiner* — Rei Tsang Shiao
(74) *Attorney, Agent, or Firm* — Knobbe, Martens, Olson & Bear, LLP

(57) ABSTRACT

Provided is a method of treating a mental disorder in a patient. Also provided is a method of enhancing a therapeutic effect of a psychedelic drug in a patient with a mental disorder. Additionally provided is a method of reducing an adverse effect of a psychedelic drug in a patient. Further provided is the use of an anxiolytic to enhance a therapeutic effect of a psychedelic drug in a patient with a mental disorder. Also provided is a method of treating cerebral palsy in a patient.

15 Claims, No Drawings

PSYCHEDELIC DRUG TREATMENT OF NEUROPSYCHIATRIC DISORDERS AND CEREBRAL PALSY

This application claims priority of U.S. Application Ser. No. 63/214,626, which was filed on Jun. 24, 2021.

BACKGROUND OF THE INVENTION

Field of the Invention

The present application generally relates to the treatment of a neuropsychiatric disorders and cerebral palsy with a psychedelic. More specifically, the application provides methods of (a) improving the treatment of a mental disorder with a psychedelic by the administration of an anxiolytic and (b) treating cerebral palsy with a psychedelic.

Description of the Related Art

The use of psychedelic drugs such as ketamine, psilocybin, lysergic acid diethylamide (LSD), mescaline, N, N-dimethyltryptamine (DMT) and ibogaine has increased in recent years to treat mental disorders such as substance use disorders (SUDs), eating disorders, post-traumatic stress disorder (PTSD), anxiety, depression, social anxiety in autistic adults; obsessive-compulsive disorder (OCD), depression; and suicidal ideation (Breeksema et al., 2020, Front Psychiatry 11:844; Schenberg, 2018, Front. Pharmacol. 9:733; Tullis, 2021, Nature 589:506-509; Tupper et al., 2015, CMAJ 187:1054-1059; Johnson and Griffiths, 2017).

In these therapies, the psychedelic drug is typically administered to achieve a non-ordinary state of consciousness (NOSC). Adverse effects of the treatment, such as intense negative feelings, increased heart rate and increased blood pressure increases, may lower the efficacy of these therapies as well as reduce patients' willingness to receive additional psychedelic treatments. They may also reduce the safety of these treatments for patients and thus make providers unwilling to administer additional psychedelic treatments. Therefore, there is a need to reduce the intensity and/or frequency of adverse effects of psychedelic drug treatment for neuropsychiatric disorders or cerebral palsy. There is also a need for treatments for cerebral palsy. In some embodiments, the disclosed invention satisfies those needs.

SUMMARY OF THE INVENTION

One aspect provides a method of treating a neuropsychiatric disorder or cerebral palsy in a patient. The method comprises administering a psychedelic drug and an anxiolytic to the patient.

Also provided is a method of enhancing a therapeutic effect of a psychedelic drug in a patient with a neuropsychiatric disorder or cerebral palsy. The method comprises treating the patient with an anxiolytic in an amount sufficient to enhance the therapeutic effect.

Additionally provided is a method of reducing an adverse effect of a psychedelic drug used to treat a neuropsychiatric disorder or cerebral palsy. The method comprises treating the patient with an anxiolytic in an amount sufficient to reduce the adverse effect.

Further provided is the use of an anxiolytic to enhance a therapeutic effect of a psychedelic drug in a patient with a neuropsychiatric disorder or cerebral palsy.

Also provided is a method of treating cerebral palsy in a patient. The method comprises administering a psychedelic drug to the patient.

More specifically, provided a method is disclosed for treating a neuropsychiatric disorder or cerebral palsy in a patient, excluding depression, anxiety, post-traumatic stress disorder (PTSD), opioid use disorder, cocaine use disorder, and post-partum depression, the method comprising administering at least one psychedelic drug and at least one anxiolytic to the patient. In this method the neuropsychiatric disorder may be obsessive compulsive disorder (OCD), suicidal ideation, an eating disorder, a neurodevelopmental disorder, a schizophrenia spectrum disorder, a psychotic disorder, catatonia, a mood disorder excluding depression, a trauma- and stressor-related disorder excluding post-traumatic stress disorder (PTSD), a dissociative disorder, a somatic symptom disorder, a feeding disorder, an elimination disorder, a bodily distress or bodily experience disorder, a sleep-wake disorder, a breathing-related sleep disorder, a parasomnia, a sexual dysfunction, gender dysphoria, a disruptive, impulse-control, and conduct disorder, a substance-related and addictive disorder excluding opioid use disorder and cocaine use disorder, a neurocognitive disorder, a personality disorder, a paraphilic disorder, a factitious disorder, or a mental or behavioral disorder associated with pregnancy, childbirth, or the puerperium, excluding post-partum depression.

Also disclosed is a method of treating depression or anxiety in a patient, the method comprising administering at least one psychedelic drug and at least one anxiolytic to the patient, with the caveat that the psychedelic is not ketamine when the anxiolytic is a benzodiazepine.

Also disclosed in a method of treating post-traumatic stress disorder (PTSD), opioid use disorder, cocaine use disorder, or post-partum depression in a patient, the method comprising administering at least one psychedelic drug and at least one anxiolytic to the patient, with the caveat that the psychedelic drug is not ketamine when the anxiolytic is selected from (i) an oxytocin receptor agonist, (ii) a combination of a psychedelic drug esketamine and an anxiolytic oxytocin receptor agonist, and (iii) a combination of a psychedelic drug MDMA and an anxiolytic oxytocin receptor agonist, if the dosage for ketamine is about 0.3 mg to about 3600 mg, the dosage for esketamine is about 28 mg to about 84 mg, the dosage range for MDMA is about 120 mg to about 400 mg, and the dosage for the oxytocin receptor agonist dosage is about 0.5 milliunit to about 10 milliunit/minute for intravenous or about 8 IU to about 24 IU for nasal spray.

Also disclosed are such methods wherein the method comprises administering a psychedelic drug, a first anxiolytic, and a second anxiolytic to the patient. Also disclosed are such methods wherein the first anxiolytic is a benzodiazepine and the second anxiolytic is an oxytocin receptor agonist. Also disclosed are such methods wherein the psychedelic drug is ketamine, esketamine (the S enantiomer of ketamine), arketamine (the R enantiomer of ketamine), psilocybin, lysergic acid diethylamide (LSD), mescaline (3,4,5-trimethoxyphenethylamine), dextromethorphan, N, N dimethyltryptamine (DMT), 5-methoxy-N, N-dimethyltryptamine (5-MeO DMT), 3, 4-methylenedioxymethamphetamine (MDMA), nitrous oxide, ibogaine or tetrahydrocannabinol (THC). Also disclosed are such methods wherein the anxiolytic is oxytocin, a benzodiazepine, hydroxyzine, baclofen, an alpha2 agonist, a muscle relaxant, an alpha blocker, or a cannabinoid.

Also disclosed is a method of treating post-traumatic stress disorder (PTSD), opioid use disorder, cocaine use disorder, or post-partum depression in a patient, the method comprising administering at least one psychedelic drug and at least one anxiolytic to the patient. Also disclosed are such methods wherein the psychedelic and/or the anxiolytic is administered intravenously, intramuscularly, subcutaneously, intranasally, orally, rectally, or sub lingually. Also disclosed are such methods wherein the psychedelic drug and the anxiolytic are administered together. Also disclosed are such methods wherein the psychedelic drug is administered before the anxiolytic. Also disclosed are such methods wherein the psychedelic drug is administered after the anxiolytic. Also disclosed are such methods wherein the psychedelic drug and the anxiolytic are administered together in a dual agent formulation. Also disclosed are such methods wherein a dosage formulation of the psychedelic drug is a delayed release and a dosage formulation of the anxiolytic drug is an immediate release.

Also disclosed is a method of enhancing a therapeutic effect of a psychedelic drug in a patient with a neuropsychiatric disorder or cerebral palsy, the method comprising treating the patient with an anxiolytic in an amount sufficient to enhance the therapeutic effect. Also disclosed are such methods wherein the therapeutic effect is a non ordinary state of consciousness (NOSC). Also disclosed are such methods wherein the anxiolytic increases positive social affect during the NOSC. Also disclosed are such methods wherein the anxiolytic reduces fear and/or anxiety caused by the psychedelic. Also disclosed are such methods wherein the neuropsychiatric disorder is depression, obsessive compulsive disorder (OCD), suicidal ideation, an eating disorder or posttraumatic stress disorder (PTSD). Also disclosed are such methods wherein the psychedelic drug is ketamine, esketamine (the S enantiomer of ketamine), arketamine (the R enantiomer of ketamine), psilocybin, lysergic acid diethylamide (LSD), mescaline (3,4,5-trimethoxyphenethylamine), dextromethorphan, N, N dimethyltryptamine (DMT), 5-methoxy-N, N-dimethyltryptamine (5-MeO DMT), 3, 4-methylenedioxymethamphetamine (MDMA), nitrous oxide, ibogaine or tetrahydrocannabinol (THC). Also disclosed are such methods wherein the psychedelic drug is ketamine and wherein the anxiolytic is oxytocin, carbetocin, a benzodiazepine, hydroxyzine, baclofen, an alpha2 agonist, a muscle relaxant, an alpha blocker, or a cannabinoid. Also disclosed are such methods wherein the anxiolytic is administered intravenously, intramuscularly, subcutaneously, rectally, intranasally, orally, or sublingually. Also disclosed are such methods wherein the psychedelic drug and the anxiolytic are administered together. Also disclosed are such methods wherein the anxiolytic is administered after the psychedelic drug only if needed to reduce fear or anxiety, or to improve the NOSC. Also disclosed are such methods wherein the psychedelic drug is administered after the anxiolytic.

Also disclosed are method of reducing an adverse effect of a psychedelic drug in a patient, the method comprises administering an anxiolytic to the patient in an amount sufficient to reduce the adverse effect. Also disclosed are such methods wherein the patient has a neuropsychiatric disorder or cerebral palsy. Also disclosed are such methods wherein the neuropsychiatric disorder is depression, obsessive compulsive disorder (OCD), suicidal ideation, an eating disorder or post traumatic stress disorder (PTSD). Also disclosed are such methods wherein the psychedelic drug is ketamine, esketamine (the S enantiomer of ketamine), arketamine (the R enantiomer of ketamine), psilocybin, lysergic acid diethylamide (LSD), mescaline (3,4,5-trimethoxyphenethylamine), dextromethorphan, N, N dimethyltryptamine (DMT), 5-methoxy-N, N-dimethyltryptamine (5-MeO DMT), 3, 4-methylenedioxymethamphetamine (MDMA), nitrous oxide, ibogaine or tetrahydrocannabinol (THC).

DETAILED DESCRIPTION OF THE PREFERRED EMBODIMENT

Certain aspects of the disclosed invention are based, at least in part, on the discovery that treatments for neuropsychiatric disorders using psychedelic drugs is more effective if an anxiolytic is also administered, since the anxiolytic reduces or eliminates anxiety, fear, and heart rate and blood pressure increases that can occur from the psychedelic drug administration.

The inventor has also found that psychedelic drugs can significantly improve muscle spasm in cerebral palsy. Therefore, the current methods also apply to the use of psychedelic drugs for cerebral palsy.

Thus, in some embodiments, methods of treating a neuropsychiatric disorder in a patient is provided. The methods comprise administering a psychedelic drug and an anxiolytic to the patient.

The extant art does not support improving the outcome of psychedelic drug treatment by using concomitant anxiolytics. Indeed, the art teaches away from the combination of psychedelics and anxiolytics. See Andrashko et al., 2020, Front Psychiatry 11:844, found that in patients receiving ketamine for depression, concomitant use of benzodiazepines dampened the antidepressant effect of ketamine. Similarly, Albott et al., 2017, J Clin Psychiatry 78:e308-e309, found that among patients with depression receiving ketamine infusions, benzodiazepine users showed a significantly longer time to antidepressant response, and a significantly shorter time to depression relapse. Further, Ford et al. (2015) reported on a patient whose antidepressant response to ketamine infusions was more robust after her benzodiazepine was withdrawn. In another study, Salloum et al., 2019, Depress Anxiety 36:235-243, compared the antidepressant effects of ketamine treatment in depressed patients with and without concurrent high anxiety and found antidepressant response to ketamine was similar in both anxious and non-anxious patients.

Taken together, these above cited references teach away from the concurrent use of anxiolytics when using a ketamine or other psychedelics to treat depression or another psychiatric disorder. However, these publications do describe instances in which patients were prescribed anxiolytics prior to beginning ketamine treatments, and in which the patients did not take the anxiolytics in close temporal association with the administration of ketamine. These publications do not describe the effects of anxiolytics administered simultaneously or very close in time to the administration of ketamine.

This method is useful for treatment of any neuropsychiatric disorder so long as the disorder can be treated with a psychedelic drug. See, e.g., Breeksema et al., 2020, Front Psychiatry 11:844; Schenberg, 2018, Front. Pharmacol. 9:733; Tullis, 2021, Nature 589:506-509; Tupper et al., 2015, CMAJ 187:1054-1059; and Johnson and Griffiths, 2017. In some embodiments, the neuropsychiatric disorder is depression, obsessive-compulsive disorder (OCD), suicidal ideation, an eating disorder or posttraumatic stress disorder (PTSD).

In some embodiments, neuropsychiatric disorders may include neurodevelopmental disorders (e.g., intellectual disabilities, communication disorders, autism spectrum disorder, attention-deficit/hyperactivity disorder, specific learning disorder and motor disorders), schizophrenia spectrum and other psychotic disorders, catatonia, mood disorders (such as bipolar disorders and depressive disorders), anxiety disorders, obsessive-compulsive disorders, trauma- and stressor-related disorders, dissociative disorders, somatic symptom and related disorders, feeding and eating disorders, elimination disorders, disorders of bodily distress or bodily experience, sleep-wake disorders, breathing-related sleep disorders, parasomnias, sexual dysfunctions, gender dysphoria, disruptive, impulse-control, and conduct disorders, substance-related and addictive disorders, neurocognitive disorders, personality disorders, paraphilic disorders, factitious disorders, and mental or behavioral disorders associated with pregnancy, childbirth, or the puerperium.

In certain embodiments, the disclosed invention also includes a method of treating depression or anxiety in a patient by administering at least one psychedelic drug and at least one anxiolytic to the patient, excluding the combination of the psychedelic drug ketamine with the anxiolytic benzodiazepine.

Additionally, in certain embodiments, the disclosed invention includes a method of treating post-traumatic stress disorder (PTSD), opioid use disorder, cocaine use disorder, or post-partum depression in a patient, by administering at least one psychedelic drug and at least one anxiolytic to the patient, excluding the combinations of psychedelic drug ketamine and an anxiolytic oxytocin receptor agonist, psychedelic drug esketamine and an anxiolytic oxytocin receptor agonist, and a combination of a psychedelic drug MDMA and an anxiolytic oxytocin receptor agonist, where the dosage range for ketamine is 0.3 mg to about 3600 mg, the dosage range for esketamine is 28 mg to about 84 mg, the dosage range for MDMA is 120 mg to about 400 mg, and the dosage range for the oxytocin receptor agonist is 0.5 milliunit to about 10 milliunit/minute for intravenous or about 8 IU to about 24 IU for nasal spray.

In some embodiments, the method of treating a neuropsychiatric disorder or cerebral palsy includes administering a psychedelic drug, a first anxiolytic, and a second anxiolytic to the patient. In specific embodiments, the two anxiolytics administered to the patient are a benzodiazepine and an oxytocin receptor agonist.

Any psychedelic drug used for treating neuropsychiatric disorders or cerebral palsy can be utilized in these methods. In some embodiments, the psychedelic drug is ketamine, esketamine (the S enantiomer of ketamine), arketamine (the R enantiomer of ketamine), psilocybin, lysergic acid diethylamide (LSD), mescaline (3,4,5-trimethoxyphenethylamine), N, N-dimethyltryptamine (DMT), 5-methoxy-N, N-dimethyltryptamine (5-MeO DMT), 3, 4-methylenedioxymethamphetamine (MDMA), dextromethorphan, nitrous oxide, ibogaine, or tetrahydrocannabinol (THC). In specific embodiments, the psychedelic drug is ketamine.

TABLE 1

| Examples of Psychedelic Drugs |
|---|
| ketamine |
| esketamine (the S enantiomer of ketamine) |
| arketamine (the R enantiomer of ketamine), |
| psilocybin |
| 3,4-methylenedioxymethamphetamine (MDMA) |
| DMT (N,N-dimethyltryptamine) |
| 5-MeO DMT (5-methoxy-N,N-dimethyltryptamine) |
| LSD (lysergic acid diethylamide) |
| ibogaine |
| mescaline (3,4,5-trimethoxyphenethylamine) |
| dextromethorphan |
| nitrous oxide |
| tetrahydrocannabinol (THC) |

In some embodiments, the absolute daily dosage for the psychedelic is between approximately 5 mg/day and approximately 500 mg/day. For example, the daily dosage for ketamine may be between approximately 6 mg/day and approximately 400 mg/day, more preferably between approximately 15 mg/day and approximately 150 mg/day. The daily dosage for esketamine (the S enantiomer of ketamine) may be between approximately 3 mg/day and approximately 400 mg/day, more preferably between approximately 7 mg/day and approximately 150 mg/day. The daily dosage for arketamine (the R enantiomer of ketamine) may be between approximately 3 mg/day and approximately 600 mg/day, more preferably between approximately 7 mg/day and approximately 200 mg/day. The daily dose for psilocybin may be between approximately 0.5 mg/day and approximately 5000 mg/day, more preferably between approximately 5 mg/day and approximately 100 mg/day. The daily dosage for lysergic acid diethylamide (LSD) may be between approximately 0.01 mg/day and approximately 0.5 mg/day, more preferably between approximately 0.05 mg/day and approximately 0.2 mg/day. The daily dosage for mescaline (3,4,5-trimethoxyphenethylamine) may be between approximately 25 mg/day and approximately 1200 mg/day, more preferably between approximately 100 mg/day and approximately 700 mg/day. The daily dosage for N, N-dimethyltryptamine (DMT), may be between approximately 0.5 mg/day and approximately 100 mg/day, more preferably between approximately 10 mg/day and approximately 70 mg/day. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The daily dosage for 3, 4-methylenedioxymethamphetamine (MDMA) may be between approximately 5 mg/day and approximately 300 mg/day, more preferably between approximately 15 mg/day and approximately 100 mg/day. The daily dosage for dextromethorphan may be between approximately 50 mg/day and approximately 1200 mg/day, more preferably between approximately 100 mg/day and approximately 600 mg/day. The daily dosage for nitrous oxide may be between approximately 4000 mg/day and approximately 100,000 mg/day, more preferably between approximately 6000 mg/day and approximately 40,000 mg/day. The daily dosage for ibogaine may be between approximately 250 mg/day and approximately 5000 mg/day, more preferably between approximately 500 mg/day and approximately 3000 mg/day. The daily dosage for tetrahydrocannabinol (THC) may be between approximately 0.2 mg/day and approximately 40 mg/day, more preferably between approximately 2 mg/day and approximately 10 mg/day.

In some embodiments, the dosage for the psychedelic is between approximately 0.1 mg/kg/day and approximately 5 mg/kg/day. For example, the dosage for ketamine may be between approximately 0.15 mg/kg/day and approximately 4 mg/kg/day, more preferably between approximately 0.375 mg/kg/day and approximately 1.5 mg/kg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. The dosage for psilocybin may be between approximately 0.0125 mg/kg/day and approximately 50 mg/kg/day, more preferably between approximately 0.125 mg/kg/day and approximately 1 mg/kg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. The dosage for N, N-dimethyltryptamine (DMT), may be between approximately 0.0125 mg/kg/day and approximately 1 mg/kg/day, more preferably between approximately 0.25 mg/kg/day and approximately 0.7 mg/kg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. The dosage for dextromethorphan may be between approximately 1.25 mg/kg/day and approximately 12 mg/kg/day, more preferably between approximately 2.5 mg/day and approximately 6 mg/kg/day. The dosage for nitrous oxide may be between approximately 100 mg/kg/day and approximately 1000 mg/kg/day, more preferably between approximately 150 mg/kg/day and approximately 400 mg/kg/day. The dosage for ibogaine may be between approximately 6.25 mg/kg/day and approximately 50 mg/kg/day, more preferably between approximately 1.25 mg/kg/day and approximately 30 mg/kg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day.

In some embodiments, for the frequency of administration of the psychedelic, the psychedelic is administered once a day, twice a day, three times a day, four times per day, one every two days, once every three days, once every four days, or once a week.

These methods can utilize any anxiolytic now known or later discovered. Non-limiting anxiolytics include oxytocin, another oxytocin receptor agonist (e.g., carbetocin, demoxytocin, lipo-oxytocin-1, merotocin, LIT-001, TC OT 39, WAY 267464; see, e.g., PCT Patent Publication WO2020252384; Hilfiger et al., 2020, Scientific Reports 10:3017), a benzodiazepine (e.g., midazolam, triazolam, alprazolam, lorazepam, chlordiazepoxide, diazepam, clonazepam), hydroxyzine, baclofen, an alpha2 agonist such as clonidine, a muscle relaxant such as cyclobenzaprine, an alpha blocker such as clonidine, or a cannabinoid (e.g., cannabidiol (CBD) or cannabinol (CBN), etc.—see, e.g., Gülck and Møller, 2020, Trends in Plant Science 25:985-1004). In specific embodiments, the anxiolytic is oxytocin.

TABLE 2

| Examples of Anxiolytics |
|---|
| oxytocin |
| CBD (cannabidiol) |
| cyclobenzaprine |
| baclofen |
| clonidine |
| hydroxyzine |
| alprazolam |
| lorazepam |
| diazepam |
| clonazepam |
| midazolam |
| chlordiazepoxide |

In some embodiments, the absolute daily dosage for the anxiolytic is between approximately 1 mg/day and approximately 300 mg/day. For example, the daily dosage for oxytocin may be between approximately 10 IU (International Units)/day and approximately 500 IU (International Units)/day, more preferably between approximately 24 IU (International Units)/day and approximately 300 IU (International Units)/day. The daily dosage for alprazolam may be between approximately 0.05 mg/day and approximately 4 mg/day, more preferably between approximately 0.25 mg/day and approximately 2 mg/day. The daily dosage for lorazepam may be between approximately 0.2 mg/day and approximately 10 mg/day, more preferably between approximately 1 mg/day and approximately 6 mg/day. The daily dosage for diazepam may be between approximately 0.25 mg/day and approximately 100 mg/day, more preferably between approximately 2 mg/day and approximately 40 mg/day. The daily dosage for clonazepam may be between approximately 0.05 mg/day and approximately 8 mg/day, more preferably between approximately 0.25 mg/day and approximately 4 mg/day. The daily dosage for midazolam may be between approximately 0.2 mg/day and approximately 20 mg/day, more preferably between approximately 0.5 mg/day and approximately 10 mg/day. The daily dosage for chlordiazepoxide may be between approximately 1 mg/day and approximately 200 mg/day, more preferably between approximately 10 mg/day and approximately 100 mg/day. The daily dosage for hydroxyzine, may be between approximately 20 mg/day and approximately 250 mg/day, more preferably between approximately 50 mg/day and approximately 150 mg/day. The daily dosage for baclofen may be between approximately 2 mg/day and approximately 125 mg/day, more preferably between approximately 10 mg/day and approximately 80 mg/day. The daily dosage for clonidine, may be between approximately 0.05 mg/day and approximately 12 mg/day, more preferably between approximately 2.0 mg/day and approximately 8 mg/day. The daily dosage for cyclobenzaprine, may be between approximately 2 mg/day and approximately 100 mg/day, more preferably between approximately 10 mg/day and approximately 50 mg/day. The daily dosage for cannabidiol (CBD) may be between approximately 0.5 mg/day and approximately 120 mg/day, more preferably between approximately 5 mg/day and approximately 60 mg/day.

In some embodiments, the dosage for the anxiolytic is between approximately 1 mg/day and approximately 300 mg/day. For example, the dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. The dosage for alprazolam may be between approximately 0.00125 mg/day and approximately 0.04 mg/kg/day, more preferably between approximately 0.00625 mg/kg/day and approximately 0.02 mg/kg/day. The dosage for lorazepam may be between approximately 0.005 mg/kg/day and approximately 0.1 mg/kg/day, more preferably between approximately 0.025 mg/kg/day and approximately 0.06 mg/kg/day. The dosage for diazepam may be between approximately 0.00625 mg/kg/day and approximately 1 mg/kg/day, more preferably between approximately 0.05 mg/kg/day and approximately 0.4 mg/kg/day. The dosage for clonazepam may be between approximately 0.00125 mg/kg/day and approximately 0.08 mg/kg/day, more preferably between approximately 0.00625 mg/kg/day and approximately 0.04 mg/kg/day. The dosage for midazolam may be between approximately 0.005 mg/kg/day and approximately 0.2 mg/kg/day, more preferably between approximately 0.0125 mg/kg/day and approximately 0.1 mg/kg/day. The dosage for chlordiazepoxide may be between approximately 0.025 mg/kg/day and approximately 2 mg/kg/day, more preferably between approximately 0.25 mg/kg/day and approximately 1 mg/kg/day. The dosage for hydroxyzine, may be between approximately 0.5 mg/kg/day and approximately 2.5 mg/kg/day, more preferably between approximately 1.25 mg/kg/day and approximately 1.5 mg/kg/day. The dosage for baclofen may be between approximately 0.05 mg/kg/day and approximately 1.25 mg/kg/day, more preferably between approximately 0.25 mg/kg/day and approximately 0.8 mg/kg/day. The dosage for clonidine, may be between approximately 0.00125 mg/kg/day and approximately 0.12 mg/kg/day, more preferably between approximately 0.05 mg/kg/day and approximately 0.08 mg/kg/day. The dosage for cyclobenzaprine, may be between approximately 0.05 mg/kg/day and approximately 1 mg/kg/day, more preferably between approximately 0.25 mg/kg/day and approximately 0.5 mg/kg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day.

In some embodiments, for the frequency of administration of the anxiolytic, the psychedelic is administered once a day, twice a day, three times a day, four times per day, one every two days, once every three days, once every four days, or once a week.

In these methods, the psychedelic and/or the anxiolytic can be administered by any route, e.g., intravenously, intramuscularly, intranasally, orally, subcutaneously, rectally or sublingually.

In some embodiments, the psychedelic drug and the anxiolytic are administered together. In other embodiments, the psychedelic drug is administered after the anxiolytic. In additional embodiments, the psychedelic drug is administered before the anxiolytic. When the psychedelic drug is administered before or after the anxiolytic, the administration of the two agents can be separated by any amount of time, e.g., 5 min., 10 min., 15 min., 20 min., 25 min., 30 min., 45 min., 1 hour, 2 hours, or any time period before, after or in between those times.

In some embodiments, the psychedelic drug and the anxiolytic are administered together in a dual agent formulation. In certain embodiments, the dosage formulation of the psychedelic drug is a delayed release and a dosage formulation of the anxiolytic drug is an immediate release in the dual agent formulation.

In some embodiments, a patient with a neuropsychiatric disorder is treated with a dual agent formulation comprising a psychedelic drug and an anxiolytic. For example, in some embodiments, the dual agent formulation is formulated for the immediate release of the anxiolytic and delayed release of the psychedelic drug.

In further embodiments, the anxiolytic is only administered if the patient is exhibiting deleterious effects (e.g., anxiety) from the psychedelic.

Additional therapeutic agents may also be administered in these methods, e.g., a second anxiolytic or any other therapeutic agent.

Also provided is a method of enhancing a therapeutic effect of a psychedelic drug in a patient with a neuropsychiatric disorder or cerebral palsy. The method comprises treating the patient with an anxiolytic in an amount sufficient to enhance the therapeutic effect.

As previously discussed, a psychedelic drug is therapeutic by inducing a non-ordinary state of consciousness (NOSC) in the patient. In these methods, the anxiolytic increases positive social affect during the NOSC, for example by reducing fear and/or anxiety caused by the psychedelic.

Consistent with the previously described methods, this method is useful for treatment of any neuropsychiatric disorders or cerebral palsy that can be treated with a psychedelic drug, e.g., depression, anxiety, obsessive-compulsive disorder (OCD), suicidal ideation, eating disorders, or post-traumatic stress disorder (PTSD). Also as with the previously described methods, any psychedelic drug used for treating neuropsychiatric disorders or cerebral palsy, e.g., ketamine, esketamine (the S enantiomer of ketamine), arketamine (the R enantiomer of ketamine), psilocybin, lysergic acid diethylamide (LSD), mescaline (3,4,5 trimethoxyphenethylamine), N, N-dimethyltryptamine (DMT), 5-methoxy-N, N-dimethyltryptamine (5-MeO DMT), 3, 4-methylenedioxymethamphetamine (MDMA), dextromethorphan, nitrous oxide, ibogaine, or tetrahydrocannabinol (THC) can be utilized in these methods. Further, any anxiolytic, now known, or later discovered, may be used in these methods. Examples include oxytocin, another oxytocin receptor agonist e.g., carbetocin, demoxytocin, lipo-oxytocin-1, merotocin, LIT 001, WAY 267464), a benzodiazepine (e.g., midazolam, triazolam, alprazolam, lorazepam, chlordiazepoxide, diazepam, clonazepam), hydroxyzine, baclofen, an alpha2 agonist such as clonidine, or a cannabinoid (e.g., cannabidiol (CBD) or cannabinol (CBN)). Routes of administration, e.g., intravenously, intramuscularly, subcutaneously intranasally, orally, rectally or sublingually, are also as previously discussed, as is the timing of the administration of the two agents, i.e., simultaneously or one before the other.

Additionally provided is a method of reducing an adverse effect of a psychedelic drug in a patient. The method comprises treating the patient with an anxiolytic in an amount sufficient to reduce the adverse effect.

In various embodiments of this method, the psychedelic drug is used to treat a neuropsychiatric disorder or cerebral palsy.

Consistent with the previously described methods, this method is useful for treatment of any neuropsychiatric disorders or cerebral palsy that can be treated with a psychedelic drug, e.g., depression, anxiety, obsessive-compulsive disorder (OCD), suicidal ideation, eating disorders, or post-traumatic stress disorder (PTSD). Also as with the previously described methods, any psychedelic drug used for treating neuropsychiatric disorders or cerebral palsy, e.g., ketamine, esketamine (the S enantiomer of ketamine), arketamine (the R enantiomer of ketamine), psilocybin, lysergic acid diethylamide (LSD), mescaline (3,4,5-trimethoxyphenethylamine), N, N-dimethyltryptamine (DMT), 5-methoxy-N, N-dimethyltryptamine (5-MeO DMT), 3, 4-methylenedioxymethamphetamine (MDMA), dextromethorphan nitrous oxide, ibogaine, or tetrahydrocannabinol (THC) can be utilized in these methods. Further, any anxiolytic, now known, or later discovered, may be used in these methods. Examples include oxytocin, another oxytocin receptor agonist (e.g. carbetocin, demoxytocin, lipo-oxytocin-1, merotocin, LIT-001, TC OT 39, WAY 267464), a benzodiazepine (e.g., midazolam, triazolam, alprazolam, lorazepam, chlordiazepoxide, diazepam, clonazepam), hydroxyzine, baclofen, an alpha2 agonist such as clonidine, a muscle relaxant such as cyclobenzaprine, an alpha blocker such as clonidine, or a cannabinoid (e.g., cannabidiol (CBD) or cannabinol (CBN). Routes of administration, e.g., intravenously, intramuscularly, subcutaneously intranasally, orally, rectally or sublingually, are also as previously discussed, as is the timing of the administration of the two agents, i.e., simultaneously or one before the other.

In certain embodiments, the disclosed invention is additionally directed to the use of an anxiolytic to enhance a therapeutic effect of a psychedelic drug in a patient with a neuropsychiatric disorders or cerebral palsy, e.g., by increasing positive social affect during the NOSC, for example by reducing fear and/or anxiety caused by the psychedelic.

Consistent with the previously described methods, treatment of any mental disorder that can be treated with a psychedelic drug is envisioned in this use, e.g., depression, obsessive-compulsive disorder (OCD), suicidal ideation, or post-traumatic stress disorder (PTSD). Also as with the previously described methods, any psychedelic drug used for treating mental disorders, e.g., ketamine, esketamine (the S enantiomer of ketamine), arketamine (the R enantiomer of ketamine), psilocybin, lysergic acid diethylamide (LSD), mescaline (3,4,5 trimethoxyphenethylamine), N, N-dimethyltryptamine (DMT), 5-methoxy-N, N-dimethyltryptamine (5-MeO DMT), dextromethorphan, 3, 4-methylenedioxymethamphetamine (MDMA), nitrous oxide, ibogaine, or tetrahydrocannabinol (THC) can be utilized here. Further, any anxiolytic, now known, or later discovered, may be used. Examples include oxytocin, another oxytocin receptor agonist (e.g., carbetocin, demoxytocin, lipo-oxytocin-1, merotocin, LIT 001, TC OT 39, WAY 267464), a benzodiazepine (e.g., midazolam, triazolam, alprazolam, lorazepam, chlordiazepoxide, diazepam, clonazepam), hydroxyzine, baclofen, an alpha2 agonist such as clonidine, a muscle relaxant such as cyclobenzaprine, an alpha blocker such as clonidine, or a cannabinoid (e.g., cannabidiol (CBD) or cannabinol (CBN)). Routes of administration, e.g., intravenously, intramuscularly, subcutaneously, rectally, intranasally, orally, or sublingually, are also as previously discussed, as is the timing of the administration of the two agents, i.e., simultaneously or one before the other.

Also provided is a method of treating cerebral palsy in a patient. The method comprises administering a psychedelic drug to the patient.

In these methods, any psychedelic drug can be utilized. In some embodiments, the psychedelic drug is ketamine, esketamine (the S enantiomer of ketamine), arketamine (the R enantiomer of ketamine), psilocybin, lysergic acid diethylamide (LSD), mescaline (3,4,5-trimethoxyphenethylamine), N, N-dimethyltryptamine (DMT), 5-methoxy-N, N-dimethyltryptamine (5-MeO DMT), dextromethorphan, 3, 4-methylenedioxymethamphetamine (MDMA), nitrous oxide, ibogaine or tetrahydrocannabinol (THC). In specific embodiments, the psychedelic drug is ketamine.

In further embodiments of these methods, an anxiolytic is also administered to the patient. As discussed in methods provided above, any anxiolytic may be administered here. In various embodiments, the anxiolytic is oxytocin, another oxytocin receptor agonist (e.g., carbetocin, demoxytocin, lipo-oxytocin-1, merotocin, LIT 001, TC OT 39, WAY 267464), a benzodiazepine (e.g., midazolam, triazolam, alprazolam, lorazepam, chlordiazepoxide, diazepam, clonazepam), hydroxyzine, baclofen, an alpha2 agonist such as clonidine, or a cannabinoid (e.g., cannabidiol (CBD) or cannabinol (CBN)).

1. In one embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, oxytocin. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

2. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, cannabidiol (CBD). The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

3. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, cyclobenzaprine. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

4. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, baclofen. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

5. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, clonidine. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

6. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, hydroxyzine. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

7. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, alprazolam. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

8. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, lorazepam. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

9. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, diazepam. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

10. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, clonazepam. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

11. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, midazolam. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

12. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ketamine and anxiolytic drug, chlordiazepoxide. The daily dosage for ketamine may be between approximately 6 mg/day and approximately 400 mg/day, more preferably between approximately 15 mg/day and approximately 150 mg/day. The dosage for ketamine may be between approximately 0.15 mg/kg/day and approximately 4 mg/kg/day, more preferably between approximately 0.375 mg/kg/day and approximately 1.5 mg/kg/day. For the frequency of administration of ketamine, ketamine may be administered once a day, twice a day, three times a day, or four times per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

13. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, oxytocin. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

14. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, cannabidiol (CBD). The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

15. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, cyclobenzaprine. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

16. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, baclofen. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

17. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, clonidine. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

18. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, hydroxyzine. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

19. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, alprazolam. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

20. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, lorazepam. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

21. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, diazepam. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

22. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, clonazepam. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

23. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, midazolam. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

24. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, esketamine (the S enantiomer of ketamine) and anxiolytic drug, chlordiazepoxide. The daily dosage for esketamine (the S enantiomer of ketamine) may be between approximately 3 mg/day and approximately 400 mg/day, more preferably between approximately 7 mg/day and approximately 150 mg/day. The dosage for esketamine (the S enantiomer of ketamine) may be between approximately 0.075 mg/kg/day and approximately 4 mg/kg/day, more preferably between approximately 0.175 mg/kg/day and approximately 1.5 mg/kg/day. For the frequency of administration of esketamine (the S enantiomer of ketamine), esketamine (the S enantiomer of ketamine) may be administered once a day, twice a day, three times a day, or four times per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

25. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, oxytocin. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

26. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, cannabidiol (CBD). The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

27. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, cyclobenzaprine. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

28. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, baclofen. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

29. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, clonidine. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

30. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, hydroxyzine. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

31. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, alprazolam. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

32. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, lorazepam. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

33. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, diazepam. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

34. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, clonazepam. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

35. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, midazolam. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

36. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, arketamine (the R enantiomer of ketamine) and anxiolytic drug, chlordiazepoxide. The daily dosage for arketamine (the R enantiomer of ketamine) may be between approximately 3 mg/day and approximately 600 mg/day, more preferably between approximately 7 mg/day and approximately 200 mg/day. The dosage for arketamine (the R enantiomer of ketamine) may be between approximately 0.075 mg/kg/day and approximately 6 mg/kg/day, more preferably between approximately 0.175 mg/kg/day and approximately 2 mg/kg/day. For the frequency of administration of arketamine (the R enantiomer of ketamine), arketamine (the R enantiomer of ketamine) may be administered once a day, twice a day, three times a day, or four times per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

37. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, oxytocin. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

38. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, cannabidiol (CBD). The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

39. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, cyclobenzaprine. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

40. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, baclofen. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

41. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, clonidine. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

42. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, hydroxyzine. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

43. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, alprazolam. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

44. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, lorazepam. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

45. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, diazepam. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

46. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, clonazepam. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

47. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, midazolam. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

48. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, psilocybin and anxiolytic drug, chlordiazepoxide. The daily dose for psilocybin may be between approximately 0.5 mg/day and approximately 5000 mg/day, more preferably between approximately 5 mg/day and approximately 100 mg/day. The dosage for psilocybin may be between approximately 0.0125 mg/kg/day and approximately 50 mg/kg/day, more preferably between approximately 0.125 mg/kg/day and approximately 1 mg/kg/day. For the frequency of administration of psilocybin, psilocybin may be administered once a day per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

49. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, oxytocin The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

50. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, cannabidiol (CBD). The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

51. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, cyclobenzaprine.

The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

52. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, baclofen. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

53. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, clonidine. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

54. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, hydroxyzine. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

55. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, alprazolam. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

56. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, lorazepam. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

57. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, diazepam. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

58. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, clonazepam. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

59. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, midazolam. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

60. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 3, 4-methylenedioxymethamphetamine (MDMA) and anxiolytic drug, chlordiazepoxide. The daily dosage for 3, 4-methylenedioxymethamphetamine (MDMA) may be between approximately 5 mg/day and approximately 300 mg/day, more preferably between approximately 15 mg/day and approximately 100 mg/day. The dosage for 3, 4-methylenedioxymethamphetamine (MDMA) may be between approximately 0.125 mg/kg/day and approximately 3 mg/kg/day, more preferably between approximately 0.375 mg/kg/day and approximately 1 mg/kg/day. For the frequency of administration of 3, 4-methylenedioxymethamphetamine (MDMA), 3, 4-methylenedioxymethamphetamine (MDMA) may be administered once a day per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

61. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, oxytocin. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

62. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, cannabidiol (CBD). The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

63. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, cyclobenzaprine. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

64. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, baclofen. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

65. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, clonidine. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

66. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, hydroxyzine. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

67. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, alprazolam. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

68. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, lorazepam. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

69. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, diazepam. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

70. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, clonazepam. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

71. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, midazolam. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

72. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, N, N-dimethyltryptamine (DMT) and anxiolytic drug, chlordiazepoxide. The daily dosage for N, N dimethyltryptamine (DMT), may be between approximately 0.5 mg/day and approximately 100 mg/day, more preferably between approximately 10 mg/day and approximately 70 mg/day. The dosage for N, N dimethyltryptamine (DMT), may be between approximately 0.0125 mg/kg/day and approximately 1 mg/kg/day, more preferably between approximately 0.25 mg/kg/day and approximately 0.7 mg/kg/day. For the frequency of administration of N, N dimethyltryptamine (DMT), N, N dimethyltryptamine (DMT) may be administered once a day, twice a day, three times a day, or four times per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

73. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, oxytocin. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO) DMT), 5-methoxy-N, N-dimethyltryptamine (5-MeO) DMT) may be administered once a day, twice a day, three times a day, or four times per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

74. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, cannabidiol (CBD). The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

75. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO) DMT) and anxiolytic drug, cyclobenzaprine. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

76. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, baclofen. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (S-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

77. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, clonidine. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

78. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, hydroxyzine. The daily dosage for 5-methoxy-N, N-dimethyltryptamine (5-MeO) DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO) DMT) may be administered once a day, twice a day, three times a day, or four times per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

79. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, alprazolam. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

80. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, lorazepam. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

81. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, diazepam. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day.

The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

82. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, clonazepam. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

83. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, midazolam. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

84. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, 5-methoxy-N, N-dimethyltryptamine (5-MeO DMT) and anxiolytic drug, chlordiazepoxide. The daily dosage for 5-methoxy-N, N-dimethyltryptamine (5-MeO DMT) may be between approximately 0.5 mg/day and approximately 120 mg/day, more preferably between approximately 0.5 mg/day and approximately 30 mg/day. The dosage for 5-methoxy-N, N-dimethyltryptamine (5-MeO DMT) may be between approximately 0.0125 mg/kg/day and approximately 1.2 mg/kg/day, more preferably between approximately 0.0125 mg/kg/day and approximately 0.3 mg/kg/day. For the frequency of administration of 5-methoxy-N, N-dimethyltryptamine (5-MeO DMT), 5-methoxy-N, N-dimethyltryptamine (5-MeO DMT) may be administered once a day, twice a day, three times a day, or four times per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

85. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, oxytocin. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

86. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, cannabidiol (CBD). The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

87. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, cyclobenzaprine. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

88. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, baclofen. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

89. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, clonidine. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

90. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, hydroxyzine. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

91. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, alprazolam. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

92. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, lorazepam. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

93. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, diazepam. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

94. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, clonazepam. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

95. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, midazolam. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

96. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, lysergic acid diethylamide (LSD) and anxiolytic drug, chlordiazepoxide. The daily dosage for lysergic acid diethylamide (LSD) may be between approximately 0.01 mg/day and approximately 0.5 mg/day, more preferably between approximately 0.05 mg/day and approximately 0.2 mg/day. The dosage for lysergic acid diethylamide (LSD) may be between approximately 0.00025 mg/kg/day and approximately 0.005 mg/kg/day, more preferably between approximately 0.00125 mg/kg/day and approximately 0.002 mg/kg/day. For the frequency of administration of lysergic acid diethylamide (LSD), lysergic acid diethylamide (LSD) may be administered once a day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/ day. For the frequency of administration of chlordiazepoxide, chlordiazepoxide may be administered once a day.

97. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, oxytocin. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

98. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, cannabidiol (CBD). The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

99. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, cyclobenzaprine. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

100. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, baclofen. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

101. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, clonidine. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

102. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, hydroxyzine. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

103. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, alprazolam. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

104. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, lorazepam. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

105. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, diazepam. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

106. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, clonazepam. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

107. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, midazolam. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

108. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, ibogaine and anxiolytic drug, chlordiazepoxide. The daily dosage for ibogaine may be between approximately 250 mg/day and approximately 5000 mg/day, more preferably between approximately 500 mg/day and approximately 3000 mg/day. The dosage for ibogaine may be between approximately 6.25 mg/kg/day and approximately 50 mg/kg/day, more preferably between approximately 1.25 mg/kg/day and approximately 30 mg/kg/day. For the frequency of administration of ibogaine, ibogaine may be administered once a day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

109. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, oxytocin. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

110. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, cannabidiol (CBD). The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

111. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, cyclobenzaprine. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

112. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, baclofen. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

113. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, clonidine. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4, 5-trimethoxyphenethylamine), mescaline (3,4,5-trimethoxyphenethylamine) may be administered once a day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

114. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, hydroxyzine. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

115. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, alprazolam. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

116. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, lorazepam. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

117. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, diazepam. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

118. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, clonazepam. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

119. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, midazolam. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

120. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, mescaline (3,4,5-trimethoxyphenethylamine) and anxiolytic drug, chlordiazepoxide. The daily dosage for mescaline (3,4,5-trimethoxyphenethylamine) may be between approximately 25 mg/day and approximately 1200 mg/day, more preferably between approximately 100 mg/day and approximately 700 mg/day. The dosage for mescaline (3,4,5-trimethoxyphenethylamine) may be between approximately 0.625 mg/kg/day and approximately 12 mg/kg/day, more preferably between approximately 2.5 mg/kg/day and approximately 7 mg/kg/day. For the frequency of administration of mescaline (3,4,5-trimethoxyphenethylamine), mescaline (3,4,5-trimethoxyphenethylamine) may be administered once a day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

121. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, oxytocin. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

122. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, cannabidiol (CBD). The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

123. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, cyclobenzaprine. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

124. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, baclofen. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

125. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, clonidine. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

126. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, hydroxyzine. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

127. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, alprazolam. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

128. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, lorazepam. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

129. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, diazepam. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/ day and approximately 1 mg/kg/day, more preferably between approximately 0.05 mg/kg/day and approximately 0.4 mg/kg/day. For the frequency of administration of diazepam, diazepam may be administered once a day.

130. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, clonazepam. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

131. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, midazolam. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

132. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, dextromethorphan and anxiolytic drug, chlordiazepoxide. The daily dosage for dextromethorphan may be between approximately 50 mg/day and approximately 1200 mg/day, more preferably between approximately 100 mg/day and approximately 600 mg/day. The dosage for dextromethorphan may be between approximately 1.25 mg/kg/day and approximately 12 mg/kg/day, more preferably between approximately 2.5 mg/day and approximately 6 mg/kg/day. For the frequency of administration of dextromethorphan, dextromethorphan may be administered once a day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

133. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, oxytocin. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

134. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, cannabidiol (CBD). The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

135. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, cyclobenzaprine. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

136. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, baclofen. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

137. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, clonidine. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

138. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, hydroxyzine. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

139. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, alprazolam. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

140. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, lorazepam. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

141. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, diazepam. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

142. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, clonazepam. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day.

143. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, midazolam. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day.

144. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, nitrous oxide and anxiolytic drug, chlordiazepoxide. The daily dosage for nitrous oxide may be between approximately 4000 mg/day and approximately 100,000 mg/day, more preferably between approximately 6000 mg/day and approximately 40,000 mg/day. The dosage for nitrous oxide may be between approximately 100 mg/kg/day and approximately 1000 mg/kg/day, more preferably between approximately 150 mg/kg/day and approximately 400 mg/kg/day. For the frequency of administration of nitrous oxide, nitrous oxide may be administered once a day, twice a day, three times a day, or four times per day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

145. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, oxytocin. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for oxytocin may be between approximately 10 IU (International Units)/day and approximately 500 IU (International Units)/day, more preferably between approximately 24 IU (International Units)/day and approximately 300 IU (International Units)/day. The dosage for oxytocin may be between approximately 0.25 IU (International Units)/kg/day and approximately 5 IU (International Units)/kg/day, more preferably between approximately 0.6 IU (International Units)/kg/day and approximately 3 IU (International Units)/kg/day. For the frequency of administration of oxytocin, oxytocin may be administered once a day.

146. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, cannabidiol (CBD). The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC)

may be administered once a day. The daily dosage for cannabidiol (CBD) may be between approximately 0.5 mg/day and approximately 120 mg/day, more preferably between approximately 5 mg/day and approximately 60 mg/day. The dosage for a cannabidiol (CBD) may be between approximately 0.0125 mg/kg/day and approximately 1.2 mg/kg/day, more preferably between approximately 0.125 mg/kg/day and approximately 0.6 mg/kg/day. For the frequency of administration of cannabidiol (CBD), cannabidiol (CBD) may be administered once a day.

147. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, cyclobenzaprine. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for cyclobenzaprine, may be between approximately 2 mg/day and approximately 100 mg/day, more preferably between approximately 10 mg/day and approximately 50 mg/day. The dosage for cyclobenzaprine, may be between approximately 0.05 mg/kg/day and approximately 1 mg/kg/day, more preferably between approximately 0.25 mg/kg/day and approximately 0.5 mg/kg/day. For the frequency of administration of cyclobenzaprine, cyclobenzaprine may be administered once a day.

148. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, baclofen. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for baclofen may be between approximately 2 mg/day and approximately 125 mg/day, more preferably between approximately 10 mg/day and approximately 80 mg/day. The dosage for baclofen may be between approximately 0.05 mg/kg/day and approximately 1.25 mg/kg/day, more preferably between approximately 0.25 mg/kg/day and approximately 0.8 mg/kg/day. For the frequency of administration of baclofen, baclofen may be administered once a day.

149. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, clonidine. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for clonidine, may be between approximately 0.05 mg/day and approximately 12 mg/day, more preferably between approximately 2.0 mg/day and approximately 8 mg/day. The dosage for clonidine, may be between approximately 0.00125 mg/kg/day and approximately 0.12 mg/kg/day, more preferably between approximately 0.05 mg/kg/day and approximately 0.08 mg/kg/day. For the frequency of administration of clonidine, clonidine may be administered once a day.

150. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, hydroxyzine. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for hydroxyzine, may be between approximately 20 mg/day and approximately 250 mg/day, more preferably between approximately 50 mg/day and approximately 150 mg/day. The dosage for hydroxyzine, may be between approximately 0.5 mg/kg/day and approximately 2.5 mg/kg/day, more preferably between approximately 1.25 mg/kg/day and approximately 1.5 mg/kg/day. For the frequency of administration of hydroxyzine, hydroxyzine may be administered once a day.

151. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, alprazolam. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for alprazolam may be between approximately 0.05 mg/day and approximately 4 mg/day, more preferably between approximately 0.25 mg/day and approximately 2 mg/day. The dosage for alprazolam may be between approximately 0.00125 mg/day and approximately 0.04 mg/kg/day, more preferably between approximately 0.00625 mg/kg/day and approximately 0.02 mg/kg/day. For the frequency of administration of alprazolam, alprazolam may be administered once a day.

152. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, lorazepam. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for lorazepam may be between approximately 0.2 mg/day and approximately 10 mg/day, more preferably between approximately 1 mg/day and approximately 6 mg/day. The dosage for lorazepam may be between approximately 0.005 mg/kg/day and approximately 0.1 mg/kg/day, more preferably between approximately 0.025 mg/kg/day and approximately 0.06 mg/kg/day. For the frequency of administration of lorazepam, lorazepam may be administered once a day.

153. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, diazepam. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for diazepam may be between approximately 0.25 mg/day and approximately 100 mg/day, more preferably between approximately 2 mg/day and approximately 40 mg/day. The dosage for diazepam may be between approximately 0.00625 mg/kg/day and approximately 1 mg/kg/day, more preferably between approximately 0.05 mg/kg/day and approximately 0.4 mg/kg/day. For the frequency of administration of diazepam, diazepam may be administered once a day.

154. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, clonazepam. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for clonazepam may be between approximately 0.05 mg/day and approximately 8 mg/day, more preferably between approximately 0.25 mg/day and approximately 4 mg/day. The dosage for clonazepam may be between approximately 0.00125 mg/kg/day and approximately 0.08 mg/kg/day, more preferably between approximately 0.00625 mg/kg/day and approximately 0.04 mg/kg/day. For the frequency of administration of clonazepam, clonazepam may be administered once a day 155. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, midazolam. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for midazolam may be between approximately 0.2 mg/day and approximately 20 mg/day, more preferably between approximately 0.5 mg/day and approximately 10 mg/day. The dosage for midazolam may be between approximately 0.005 mg/kg/day and approximately 0.2 mg/kg/day, more preferably between approximately 0.0125 mg/kg/day and approximately 0.1 mg/kg/day. For the frequency of administration of midazolam, midazolam may be administered once a day.

156. In another embodiment, a patient with a neuropsychiatric disorder or cerebral palsy, excluding depression, anxiety, post-traumatic stress disorder (PTSD), opioid use disorder, cocaine use disorder, and post-partum depression, is treated with psychedelic drug, tetrahydrocannabinol (THC) and anxiolytic drug, chlordiazepoxide. The daily dosage for tetrahydrocannabinol (THC) may be between approximately 0.2 mg/day and approximately 40 mg/day, more preferably between approximately 2 mg/day and approximately 10 mg/day. The dosage for tetrahydrocannabinol (THC) may be between approximately 0.005 mg/kg/day and approximately 0.4 mg/kg/day, more preferably between approximately 0.05 mg/kg/day and approximately 0.1 mg/kg/day. For the frequency of administration of tetrahydrocannabinol (THC), tetrahydrocannabinol (THC) may be administered once a day. The daily dosage for chlordiazepoxide may be between approximately 1 mg/day and approximately 200 mg/day, more preferably between approximately 10 mg/day and approximately 100 mg/day. The dosage for chlordiazepoxide may be between approximately 0.025 mg/kg/day and approximately 2 mg/kg/day, more preferably between approximately 0.25 mg/kg/day and approximately 1 mg/kg/day. For the frequency of administration of chlordiazepoxide, chlordiazepoxide may be administered once a day.

Anxiolytic Benefits during Treatment with Psychedelics: Treatment of Cerebral Palsy with Psychedelics 157. In one instance a female patient with depression was given ketamine and had an unpleasant experience and did not benefit therapeutically. On another day the same patient was given a 0.5 mg dose of alprazolam before the same dose of ketamine and had a more positive experience and had significant improvement in depression.

158. In another instance a male patient with depression was given a 1 mg dose of lorazepam prior to ketamine for several treatments and experienced an antidepressant effect. Then, on one occasion ketamine was given without lorazepam and the patient experienced a reduced antidepressant effect compared to the times lorazepam was administered along with the ketamine.

159. In another instance a patient with depression and suicidal ideation was given ketamine several times at different intramuscular doses (0.25-1.0 mg/kg) but did not experience improvement in depression or suicidal ideation. On another occasion the same patient was given oxytocin 40 IU intranasally 30 minutes before ketamine within that same dose range and experienced a reduced severity of depression and suicidal ideation.

160. In another instance, a male patient in his twenties with muscle spasm associated with cerebral palsy was given intramuscular ketamine (0.2-1.2 mg/kg) and experienced reduction in his muscle spasm after the treatment.

Treatment of Neuropsychiatric Disorders or Cerebral Palsy with a Psychedelic Drug and an Anxiolytic 161. In one instance, a patient with depression is treated with psychedelic drug ketamine and anxiolytic drug oxytocin.

162. In another instance, a patient with anxiety is treated with psychedelic drug ketamine and anxiolytic drug oxytocin.

163. In another instance, a patient with obsessive-compulsive disorder (OCD) is treated with psychedelic drug ketamine and anxiolytic drug oxytocin.

164. In another instance, a patient with suicidal ideation is treated with psychedelic drug ketamine and anxiolytic drug oxytocin.

165. In another instance, a patient with an eating disorder is treated with psychedelic drug ketamine and anxiolytic drug oxytocin.

166. In another instance, a patient with post-traumatic stress disorder (PTSD) is treated with psychedelic drug, ketamine and anxiolytic drug oxytocin, excluding where the dosage range for ketamine is 0.3 mg to about 3600 mg and the dosage range for oxytocin is 0.5 milliunit to about 10 milliunit/minute for intravenous or about 8 IU to about 24 IU for nasal spray.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

As used herein, in particular embodiments, the terms “about” or “approximately” when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles “a” and “an,” as used herein in the specification and in the embodiments, unless clearly indicated to the contrary, should be understood to mean “at least one.” The phrase “and/or,” as used herein in the specification and in the embodiments, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements can optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the embodiments, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the embodiments, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of” “Consisting essentially of,” when used in the embodiments, shall have its ordinary meaning as used in the field of patent law.

As used herein in the specification and in the embodiments, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method of treating a neuropsychiatric disorder or cerebral palsy in a patient, the method comprising administering at least one psychedelic drug and at least one anxiolytic to the patient, wherein:

(i) the at least one psychedelic drug is selected from the group consisting of ketamine, esketamine (the S enantiomer of ketamine), arketamine (the R enantiomer of ketamine), psilocybin, lysergic acid diethylamide (LSD), mescaline (3,4,5-trimethoxyphenethylamine), dextromethorphan, N, N dimethyltryptamine (DMT), 5-methoxy-N, N-dimethyltryptamine (5-MeO DMT), 3, 4-methylenedioxymethamphetamine (MDMA), nitrous oxide, ibogaine, and tetrahydrocannabinol (THC);

(ii) the at least one anxiolytic is selected from the group consisting of oxytocin, a benzodiazepine, hydroxyzine, baclofen, an alpha2 agonist, a muscle relaxant, an alpha blocker, and a cannabinoid;

(iii) the neuropsychiatric disorder is selected from the group consisting of obsessive compulsive disorder (OCD), suicidal ideation, an eating disorder, a neurodevelopmental disorder, a schizophrenia spectrum disorder, a psychotic disorder, catatonia, a mood disorder, a trauma- and stressor-related disorder, a dissociative disorder, a somatic symptom disorder, a feeding disorder, an elimination disorder, a bodily distress or bodily experience disorder, a sleep-wake disorder, a breathing-related sleep disorder, a parasomnia, a sexual dysfunction, gender dysphoria, a disruptive, impulse-control, and conduct disorder, a substance-related and addictive disorder, a neurocognitive disorder, a personality disorder, a paraphilic disorder, a factitious disorder, or a mental or behavioral disorder associated with pregnancy, childbirth, and the puerperium; and the neuropsychiatric disorder is not depression, anxiety, post-traumatic stress disorder (PTSD), opioid use disorder, cocaine use disorder, or post-partum depression.

2. The method of claim 1, wherein the method comprises administering a psychedelic drug, a first anxiolytic, and a second anxiolytic to the patient.

3. The method of claim 2, wherein the first anxiolytic is a benzodiazepine and the second anxiolytic is an oxytocin receptor agonist.

4. The method of claim 1, wherein the at least one psychedelic and/or the at least one anxiolytic is administered intravenously, intramuscularly, subcutaneously, intranasally, orally, rectally, or sub lingually.

5. The method of claim 1, wherein the at least one psychedelic drug and the at least one anxiolytic are administered together.

6. The method of claim 1, wherein the at least one psychedelic drug is administered before the anxiolytic.

7. The method of claim 1, wherein the at least one psychedelic drug is administered after the anxiolytic.

8. The method of claim 5, wherein the at least one psychedelic drug and the at least one anxiolytic are administered together in a dual agent formulation.

9. The method of claim 8, wherein a dosage formulation of the at least one psychedelic drug is a delayed release dosage form and a dosage formulation of the at least one anxiolytic drug is an immediate release dosage form.

10. A method of enhancing a therapeutic effect of a psychedelic drug in a patient with a neuropsychiatric disorder or cerebral palsy, the method comprising treating the patient with an anxiolytic in an amount sufficient to enhance the therapeutic effect, wherein:

(i) the at least one psychedelic drug is selected from the group consisting of ketamine, esketamine (the S enantiomer of ketamine), arketamine (the R enantiomer of ketamine), psilocybin, lysergic acid diethylamide (LSD), mescaline (3,4,5-trimethoxyphenethylamine), dextromethorphan, N, N dimethyltryptamine (DMT), 5-methoxy-N, N-dimethyltryptamine (5-MeO DMT), 3, 4-methylenedioxymethamphetamine (MDMA), nitrous oxide, ibogaine, and tetrahydrocannabinol (THC);

ii) the at least one anxiolytic is selected from the group consisting of oxytocin, a benzodiazepine, hydroxyzine, baclofen, an alpha2 agonist, a muscle relaxant, an alpha blocker, and a cannabinoid; and iii) the therapeutic effect is a non ordinary state of consciousness (NOSC).

11. The method of claim 10, wherein the anxiolytic increases positive social affect during the NOSC.

12. The method of claim 1, wherein the neuropsychiatric disorder is obsessive compulsive disorder (OCD), suicidal ideation, or an eating disorder.

13. A method of reducing an adverse effect of a psychedelic drug in a patient, the method comprises administering an anxiolytic after the psychedelic drug to the patient in an amount sufficient to reduce the adverse effect, wherein:

(i) the at least one psychedelic drug is selected from the group consisting of ketamine, esketamine (the S enantiomer of ketamine), arketamine (the R enantiomer of ketamine), psilocybin, lysergic acid diethylamide (LSD), mescaline (3,4,5-trimethoxyphenethylamine), dextromethorphan, N, N dimethyltryptamine (DMT), 5-methoxy-N, N-dimethyltryptamine (5-MeO DMT), 3, 4-methylenedioxymethamphetamine (MDMA), nitrous oxide, ibogaine, and tetrahydrocannabinol (THC);

(ii) the at least one anxiolytic is selected from the group consisting of oxytocin, a benzodiazepine, hydroxyzine, baclofen, an alpha2 agonist, a muscle relaxant, an alpha blocker, and a cannabinoid;

(iii) the patient has a neuropsychiatric disorder or cerebral palsy; and (iv) the adverse effect is fear or anxiety.

14. The method of claim 1, wherein the at least one psychedelic is in a dosage form and the at least one anxiolytic is in a separate dosage form.

15. The method of claim 1, wherein the neuropsychiatric disorder is a mood disorder, and wherein the mood disorder is a bipolar disorder.

* * * * *